(12) United States Patent
Bortlik et al.

(10) Patent No.: US 8,795,743 B2
(45) Date of Patent: Aug. 5, 2014

(54) NATURAL LYCOPENE CONCENTRATE AND METHOD FOR PRODUCTION THEREOF

(71) Applicant: Nestec S.A., Vevey (CH)

(72) Inventors: Karlheinz Bortlik, Savigny (CH); Eliane Duruz, Epalinges (CH); Eric Kolodziejezyk, Vevey (CH); Marie-Rose Fernandez-Graf, Pully (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 13/938,872

(22) Filed: Jul. 10, 2013

(65) Prior Publication Data

US 2013/0296420 A1  Nov. 7, 2013

Related U.S. Application Data

(62) Division of application No. 13/252,267, filed on Oct. 4, 2011, now Pat. No. 8,507,014, which is a division of application No. 10/568,704, filed as application No. PCT/EP2004/009349 on Aug. 20, 2004, now abandoned.

(30) Foreign Application Priority Data

Aug. 21, 2003  (EP) .................... 03018982

(51) Int. Cl.
*A61K 36/00* (2006.01)
*A61Q 19/08* (2006.01)
*A61Q 17/04* (2006.01)
*A61K 8/97* (2006.01)
*A23L 1/275* (2006.01)
*A61K 8/31* (2006.01)

(52) U.S. Cl.
CPC . *A61K 8/31* (2013.01); *A61Q 19/08* (2013.01); *A61Q 17/04* (2013.01); *A61K 8/97* (2013.01); *A23L 1/2753* (2013.01)

USPC .......................................................... 424/725

(58) Field of Classification Search
None
See application file for complete search history.

(56) References Cited

U.S. PATENT DOCUMENTS

| | | | |
|---|---|---|---|
| 2,890,231 A * | 6/1959 | Heritage et al. ................ 554/19 |
| 2,938,893 A * | 5/1960 | Gray et al. .................... 530/500 |
| 5,837,311 A | 11/1998 | Zelkha et al. |
| 5,871,574 A | 2/1999 | Kawaragi et al. |
| 6,224,876 B1 | 5/2001 | Kesharlal et al. |
| 2002/0012714 A1 | 1/2002 | Olson |
| 2002/0107292 A1 | 8/2002 | Bortlik et al. |
| 2003/0027772 A1 | 2/2003 | Breton |

FOREIGN PATENT DOCUMENTS

| | | |
|---|---|---|
| EP | 1051918 | 11/2000 |
| EP | 1103579 | 5/2001 |
| JP | 54024940 | 2/1979 |
| JP | 08154600 A * | 6/1996 |
| JP | 8336376 | 12/1996 |
| JP | 2000229827 | 8/2000 |
| WO | 0240003 | 5/2002 |
| WO | 3041678 | 5/2003 |

OTHER PUBLICATIONS

Stoyanova et al, Contents of some biologically active substances in the twigs of coniferous tree species. Study, conservation and utilisation of forest resources. Proceedings of the Third Balkan Scientific Conference, Sofia, Bulgaria, Oct. 2-6, 2001. Volume II (2002), pp. 302-310.*

Hamm et al., Vitamin C. content of thirty-six varieties of tomatoes, FASAEB Journal (1993), vol. 7, No. 3-4, p. A742.

* cited by examiner

*Primary Examiner* — Qiuwen Mi
(74) *Attorney, Agent, or Firm* — K&L Gates LLP

(57) ABSTRACT

Natural lycopene concentrate obtained from a plant structure after alkalinization, solid-liquid separation, acidification and a second solid-liquid separation. The concentrate obtained is highly bioavailable and water-soluble at room temperature.

5 Claims, No Drawings

NATURAL LYCOPENE CONCENTRATE AND METHOD FOR PRODUCTION THEREOF

PRIORITY CLAIM

This application is a divisional of U.S. patent application Ser. No. 13/252,267, filed on Oct. 4, 2011, which is a divisional of U.S. patent application Ser. No. 10/568,704, filed on Feb. 16, 2006, which is the U.S. national stage designation of International Application No. PCT/EP04/009349 filed Aug. 20, 2004, which claims priority to EP030189823 filed Aug. 21, 2003, the entire disclosures of which are incorporated by reference.

BACKGROUND

The present invention relates to a natural lycopene concentrate and its process of production and its use.

Lycopene is a natural pigment contained in a large quantity in tomatoes, but it is also present in melon, guava, watermelon or grapefruit. It is known for its bioactive properties, and in particular for its antioxidant role.

Lycopene-containing preparations exist on the market. These preparations are generally in the form of oleoresins and the lycopene which they contain is of a relatively limited bioavailability. Furthermore, the lycopene is extracted with the aid of organic solvents; the said solvents are therefore likely to be found in the form of traces in the finished product.

Indeed, EP 1103579 describes a mixture of lycopene with a solution of serum proteins in order to increase its bioavailability. The lycopene described is extracted by means of a solvent.

WO 03/041678 describes a lycopene with an increased bioavailability by virtue of the addition of various additives such as oils or surfactants. The lycopene described is extracted with solvents.

Moreover, JP 54024940 describes a process for concentrating lycopene from residues of tomatoes, such as the seeds or the skin. This process uses the endogenous enzymes of these residues in order to degrade the biological tissues and to facilitate the extraction of lycopene. This enzymatic activity is induced by an incubation of 5 hours at temperatures of between 45 and 60° C. The lycopene is then extracted after separation of the skins and seeds by filtration followed by fractional flocculation of the various undesirable insolubles.

SUMMARY

The aim of the present invention is to provide a "natural" product with increased bioavailability, that is to say that the product has only been subjected to technological treatments which do not modify its native characteristics.

Furthermore, the process of extraction according to the invention is simple, rapid and economical and at no time subject to the state of viability of the endoenzymes of the raw material.

The present invention relates to a natural lycopene concentrate, which is water-soluble at room temperature while lycopene was up until now fat-soluble. This water-solubility is obtained without adding surfactants.

The concentrate may be obtained from any lycopene-containing plant, namely: tomato, melon, watermelon, guava, grapefruit, apricot, rosehip.

In the case of tomato, the raw material used may be a tomato paste.

The expression tomato paste in the present description is understood to mean a concentrated tomato extract including proteins, carbohydrates, polysaccharides, fat-soluble compounds such as carotenoids and inter alia lycopene, and organic acids.

In the composition according to the invention, the tomato paste is chosen according to its initial lycopene concentration. Indeed, the lycopene content of the concentrate depends on the initial content of this same compound in the raw material.

Additional features and advantages are described herein, and will be apparent from, the following Detailed Description.

DETAILED DESCRIPTION

The concentrate according to the invention contains at least 1 mg of lycopene per g of the said concentrate. The concentrate preferably contains between 1 mg and 40 mg of lycopene per g of concentrate and more preferably between 10 and 30 mg of lycopene per g of concentrate.

The concentrate additionally contains up to 30% of proteins, up to 30% of polysaccharides, up to 10% of organic acids, at least 30% of lipid compounds and therefore between 0.0001 and 2% of lycopene and more preferably between 0.001 and 1% of lycopene.

The percentages are given relative to the dry weight.

The composition according to the invention may be provided in pulverulent, liquid or gel form.

In the case of the concentrate in liquid form, the said concentrate contains at least 35% of water. The said concentrate contains more preferably from 60 to 95% of water.

As mentioned above, the two important characteristics of this invention are having a lycopene concentrate having a satisfactory bioavailability, and being easy to use since, in the case of the powder, the concentrate is a lycopene powder which is water-soluble at room temperature, this being without using a solvent during the process in order to preserve the natural nature of the product in order to provide the consumer with a concentrate with a high bioactivity.

The better bioavailability of the lycopene concentrate according to the invention is explained by the fact that the crystals obtained according to the process claimed have a size which is 5 to 10 times smaller than that of the crystalline forms of oleoresin. Without forgetting that the raw material used, in this case tomato paste, is the source in which lycopene is more bioavailable because of the various technological treatments to which it is subjected during its manufacture.

The expression oleoresin is understood to mean a plant lipid extract containing carotenoids, such as lycopene, triglycerides, phospholipids, tocopherol and other more minor compounds.

The powder or the gel or the solution according to the invention may additionally contain vitamin E and/or vitamin C which could be added.

The present invention also relates to the process for manufacturing the concentrate described above in which:

- a plant structure containing a lipophilic compound is alkalinized,
- the alkalinized solution is heated to boiling temperature and maintained for 1 to 60 minutes,
- the fibres and various insoluble compounds are isolated by solid-liquid separation and preferably by filtration in the hot state,
- the solution obtained is acidified,
- the carbohydrates and other soluble compounds are isolated by solid-liquid separation and preferably by centrifugation.

The expression plant structure is understood to mean a paste of the said plant obtained by reducing its water content.

According to a first embodiment of the process, a liquid is obtained. This liquid has a rheofluidizing behaviour and its viscosity is 90 to 120 mPa.s under a shear rate of $160\ s^{-1}$. This viscosity was measured at a constant temperature of 20.5° C. with a RheoStress 150 apparatus having a Couette geometry with a shear rate increasing from 1 to $1000\ s^{-1}$.

It is possible to treat the said liquid by adding calcium in order to obtain a gel because this addition will have the effect of a gelling of the polysaccharides. In a second embodiment of the process, it is possible to dry the concentrate by spray-drying or freeze-drying in order to obtain a powder.

The composition according to the invention may be used directly in these different forms or as a mixture.

It is possible to use a tomato paste containing a minimum of 0.1 mg of lycopene per g of product at a pH between 3.5 and 5 and more preferably between 4 and 4.5. This paste is alkalinized with demineralized water and a base of the NaOH type until a pH of between 6 and 9 is obtained.

This preparation is mixed while heating to the boiling temperature. This boiling is maintained for 1 to 60 minutes and more preferably for 2 to 30 minutes.

A solid-liquid separation is then carried out in order to isolate the fibres and other insoluble compounds and a filtration in the hot state is more preferably carried out.

The filtrate recovered is a solution containing dispersed lycopene. It is acidified with an acid of the citric acid type to a pH of between 3.5 and 5 and more preferably between 4 and 4.5.

This preparation is mixed and then a solid-liquid separation is carried out in order to recover the carbohydrates and other soluble compounds and a centrifugation is more preferably carried out.

The solution obtained is a lycopene concentrate according to the invention. It is possible to bring the pH to neutrality with demineralized water and a base of the NaOH type, while simultaneously mixing.

The lycopene is now water-soluble because it has formed a complex with proteins of the medium and with polysaccharides.

Depending on the desired physical form, the lycopene concentrate is either used as it is, in this case in liquid form, or in gel form; calcium will then be added to the complex in order to cause gelling of the polysaccharides.

Finally, in order to obtain a powder, the concentrate is dried by spray-drying or any other means known to persons skilled in the art.

The present invention also relates to the use of the powder described above in a cosmetic composition in order to slow the ageing of the skin and/or the skin damage caused by exposure to UV, the said composition containing at least $10^{-10}\%$ of lycopene.

This composition, which can be used by the topical route, may additionally contain a cosmetically acceptable fat or oil. The addition of other active cosmetic ingredients is also possible. The composition may also contain a structuring agent, a surfactant, excipients, colorants, perfumes, abrasives or opacifiers.

The composition according to the invention contains between $10^{-10}$ and 10% of lycopene, more preferably a cosmetic composition contains between $10^{-8}$ and 5% of lycopene.

The present invention also relates to the use of the lycopene concentrate in compositions which can be ingested orally in order to use the high bioavailability of the lycopene in this form. The aim is to induce photoprotection and to slow the ageing of the skin. The media which are likely to contain this concentrate may be: drinks, chocolate, ice creams, cereal preparations, soluble coffee and prepared meals.

In this case, the powder is dissolved in the relevant preparations so as to have a daily intake of between 0.001 and 50 mg of lycopene. The preferred daily intake will be between 2 mg and 10 mg.

The present invention may also be provided in the form of pills, gelatin capsules or tablets containing doses of 0.001 to 100% of the said concentrate. These products may then be ingested directly with water or by any other known means.

The concentrate may finally be envisaged as a product which prevents skin conditions linked to excessive exposure to UV. In this case, the use may be both by the oral and topical routes.

The remainder of the description is now made with reference to the examples:

By way of example and not limitation, examples of the present invention are as follows:

EXAMPLE 1

Preparation of the Concentrate in Powdered Form:

50 kg of tomato purée at pH 4.3 are mixed with 100 kg of demineralized water in a batch. This mixing is carried out at a temperature of 25° C. The pH is brought to 7 with NaOH.

The solution is heated to boiling temperature and this boiling is maintained for 5 minutes.

The solution is allowed to stand for 15 minutes at room temperature, then filtered in the hot state in a Westfalia type decanter.

The filtrate collected is cooled in water at a temperature of 15° C. This solution is mixed while acidifying with citric acid to a pH of 4.3.

The solution is then centrifuged in a Padberg type centrifuge at 14 000 revolutions per minute.

The supernatant is recovered and its pH is adjusted to 7.00 with NaOH.

Finally, the solution obtained is spray-dried in a NIRO type spray-dryer with an inlet temperature of 110 to 130° C. and an outlet temperature of between 70 and 80° C. The speed of rotation of the spray-drying nozzle is between 24 000 and 30 000 revolutions per minute depending on the desired powder fineness.

The concentrate according to the invention is then recovered.

EXAMPLE 2

Cosmetic Composition:

A facial milk is prepared which contains 7% of liquid paraffin, 2% of powder according to Example 1, 3% of glyceryl monostearate, polyethylene glycol stearate, 0.4% of carboxyvinyl polymer, 0.7% of stearyl alcohol, 3% of soya-bean proteins, 0.4% of NaOH, a preservative and the balance to 100 is water.

EXAMPLE 3

Cosmetic Composition

A facial gel is prepared which contains 10% of glycerin, 2% of powder according to Example 1, 1% of disodium cocoamphodiacetate, a preservative and the balance to 100 is water.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method for preparing a concentrate, the method comprising:
   alkalinizing a plant structure containing a lipophilic compound;
   heating the alkalinized solution to boiling temperature and maintaining the boiling temperature for 1 to 60 minutes;
   isolating fibres and various insoluble compounds by solid-liquid separation;
   acidifying a complex obtained; and
   isolating carbohydrates and other soluble compounds by solid-liquid separation to obtain the concentrate, wherein the concentrate comprises between 1 mg and 40 mg of lycopene per g of concentrate.

2. The method of claim 1, wherein the concentrate comprises between 10 and 30 mg of lycopene per g of concentrate.

3. The method of claim 1 comprising the step of adding calcium to the complex to obtain a gel.

4. The method of claim 1 comprising the step of drying an emulsion by spray-drying or freeze-drying in order to obtain a powder.

5. The method of claim 1, wherein the concentrate is in a form selected from the group consisting of pulverulent, liquid and gel form.

* * * * *